United States Patent [19]

Cavazza et al.

[11] Patent Number: 5,591,450
[45] Date of Patent: Jan. 7, 1997

[54] L-CARNITINE SALT AND COMPOSITIONS CONTAINING SAME

[75] Inventors: Claudio Cavazza; Paolo Cavazza, both of Rome, Italy

[73] Assignee: Advantgarde S.p.A., Rome, Italy

[21] Appl. No.: 473,208

[22] Filed: Jun. 7, 1995

[30] Foreign Application Priority Data

Jun. 20, 1994 [IT] Italy ................... RM94A0396

[51] Int. Cl.$^6$ ................ A61K 9/14; A61K 9/20; A61K 9/48; A61K 31/225
[52] U.S. Cl. ............ 424/451; 424/464; 424/489; 514/547; 562/567
[58] Field of Search ................... 424/464, 451, 424/489; 514/547; 562/567

[56] References Cited

U.S. PATENT DOCUMENTS 4,968,719  11/1990  Brevetti ..................... 514/556
5,137,910  8/1992  Gray et al. ................ 514/419

Primary Examiner—James M. Spear
Attorney, Agent, or Firm—Oblon, Spivak, McClelland, Maier & Neustadt, P.C.

[57] ABSTRACT

L-carnitine glycolate, a novel stable and non-hygroscopic salt of L-carnitine and the use thereof for preparing orally administrable, particularly solid compositions in the form of pills, tablets, troches, capsules, powders and the like, are disclosed.

8 Claims, No Drawings

L-CARNITINE SALT AND COMPOSITIONS CONTAINING SAME

The present invention relates to a novel L-carnitine salt and the use thereof for producing orally administrable, particularly solid, compositions in the form of pills, tablets, troches, capsules, powders and the like.

It is well known that L-carnitine lends itself to various therapeutical uses.

For instance, L-carnitine has been used in the cardiovascular field in the treatment of acute and chronic myocardial ischaemia, angina pectrois, cardiac arrhythmias and insufficiency. In nephrology, L-carnitine has been administered to chronic uraemic patients who are subject to regular haemodialysis treatment with a view to counteracting muscular asthenia and the onset of muscular cramps.

Further therapeutical uses are the restoration of HDL/LDL+VLDL ratio to normal and in total parenteral nutrition.

It is also known that the salts of carnitine possess the same therapeutical activities as those of the so-called "inner salt" and can, therefore, be used in place thereof, provided that they are "pharmacologically acceptable" salts. So, practically, the choice between the "inner salt" and a true carnitine salt depends mostly on which compound is more easily or economically available and on pharmaceutical technology considerations rather than on therapeutical activity considerations. Thus, for instance, (see U.S. Pat. No. 4,968,719) suitable pharmaceutically acceptable salts include the acid addition salts and may contain as the anion: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethane-sulfonate, lactate, maleate, methanesulfonate, 2-naphtalenesulfonate, nicotinate, oxalate, palmitate, pectinate, persulfate, 3-phenylpropionate, picrate, pivalate, propionate, succinate, tartrate, thiocyanate, tosylate, undecanoate and the like.

Recently, an increasing number of non-ethical, over-the-counter L-carnitine-containing preparations have reached the market, following full scientifically-grounded recognition that in athletes L-carnitine markedly contributes to supplying the muscle with energy and improves endurance and stress tolerance. Moreover, L-carnitine is an indispensable nutritional supplement for vegetarians whose diets are low in carnitine and in the two aminoacids (lysine and methionine) which are the precursors for L-carnitine biosynthesis in human liver and kidneys.

Consequently, among such consumers the need for suitable forms of administration, particularly of orally administrable preparations and preferably of solid formulations, has developed.

As known, L-carnitine inner salt is a highly hygroscopic compound and, consequently, cannot be easily storaged, handled end compounded, particularly with regard to the manufacture of solid administration forms. Moreover, L-carnitine often presents an unpleasant fishy odour because of the presence of traces of trimethylsmine.

The problem of converting L-carnitine into non hygroscopic, pharmaceutically acceptable salts has been already tackled. For instance, EP 0 150 688 discloses the preparation of some of such salts, e.g. L-carnitine acid fumarate.

It is the object of this invention to provide a novel non-hygroscopic, stable and odourless pharmaceutically acceptable salt of L-carnitine, namely L-carnitine glycolate which has formula (I)

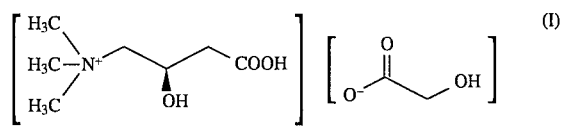

This novel salt can be easily, storaged and processed into stable solid orally administrable preparations particularly suitable for athletes and vegetarians nutritional supplements. This is quite surprising since glycolic acid is somewhat hygroscopic.

L-carnitine glycolate can be prepared as follows:

EXAMPLE

Preparation of L-carnitine glycolate (ST 1136).

L-carnitine inner salt (16.1 g; 0.1 moles) was dissolved in 100 mL $H_2O$, Glycolic acid (7.6 g; 0.1 moles) was added to the solution.

The resulting solution was concentrated under vacuum at 40° C. The residue was taken up with isopropanol and the solid residue filtered off. 23 g were obtained.

The compound was crystallized from hot isopropanol.

| M.P. = 112.3° C. (DSC) Elemental analysis $C_9H_{17}NO_6$ | | | |
|---|---|---|---|
| | C % | H % | N % |
| Calculated | 45.95 | 7.28 | 5.95 |
| Found | 46.17 | 8.46 | 6.06 |
| Water content 0.3% | | | |
| pH = 3.9 | | | |
| $[\alpha]_D^{25} = -19.9°$ (c = 1%, $H_2O$) | | | |

HPLC

Column: μ Bondapack-$NH_2$ (10 μm) 300 mm×3.9 mm

Temperature: 30° C.

Mobile phase: $CH_3CN/KH_2PO_4$ mM pH 5.2 65/35

Flow rate: 1.0 ml/min

Glycolic acid $R_t$=4.91 min 31.6%

L-carnitine $R_t$=8.99 min 68.4%

NMR $D_2O$ δ4.5–4.4(1H,m,$\underline{CH}OH$); 3.9(2H,s,$\underline{CH_2}OH$); 3.3(2H,m,$CH_2N+$); 3.1(9H,s,$(CH_3)_3N+$); 2.4(2H,dd,$CH_2COO$)

Hygroscopicity tests were carried out on L-carnitine glycolate and, for comparison sake, on the highly hygroscopic L-carnitine inner salt and two known, non-hygroscopic L-carnitine salts, namely L-carnitine L-tartrate (see Müller et al., Hoppe-Seyler's Z. Phisiol. Chem. 353, 618–622, 1972) and L-carnitine acid fumarate (see EP 150 688). Samples of the aforesaid salts were exposed to a 90% humidity environment, at 25° C., and their Karl Fisher index (K.F.) was measured at various times.

| | Karl Fisher index after | | | | |
|---|---|---|---|---|---|
| | 0 hours | 16 hours | 24 hours | 40 hours | 112 hours |
| L-carnitine inner salt | 0.20 | 3.40 | 4.40 | 7.60 | 12.90 |
| L-carnitine L-tartrate | 0.30 | 0.30 | 0.30 | 0.30 | 0.50 |

| | Karl Fisher index after | | | | |
|---|---|---|---|---|---|
| | 0 hours | 16 hours | 24 hours | 40 hours | 112 hours |
| L-carnitine acid fumarate | 0.50 | 0.50 | 0.75 | 0.82 | 0.91 |
| L-carnitine glycolate | 0.30 | 0.50 | 0.50 | 0.50 | 0.50 |

According to the present invention, the tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; a sweetening agent such as sucrose or saccharin or flavorings agent such as peppermint, methyl salicylate, or orange flavouring. When the dosage unit form is a capsule it may contain, in addition to material of the above type, a liquid carrier such as a fatty oil. Other dosage unit forms may contain other various materials which modify the physical form of the dosage unit, for example, coatings. Thus tablets or pills may be Coated with sugar, shellac, or other enteric coating agents. A syrup may contain, in addition to the active compound, sucrose as a sweetening agent and certain preservatives, dyes and colorings and flavors. Materials used in preparing these various compositions should be pharmaceutically pure and non-toxic in the amounts used.

We claim:

1. L-carnitine glycolate.

2. An orally administrable composition comprising L-carnitine glycolate and a pharmaceutically acceptable carrier or excipient thereof.

3. The composition of claim 2 as a solid composition.

4. The composition of claim 3 in the form of a pill, tablet, troche, capsule or powder.

5. The composition of claim 4 which further comprises at least one member selected from the group consisting of a binder, disintegrating agent, lubricant, glidant, flow regulating agent, sweetening agent and flavouring agent.

6. A method of preparing an L-carnitine glycolate composition, comprising:

combining L-carnitine glycolate with a pharmaceutically acceptable excipient.

7. The method of claim 6, wherein the composition is an orally administratable solid composition.

8. The method of claim 7, wherein the composition is in the form of pills, tablets, troches, capsules or a powder.

* * * * *

UNITED STATES PATENT AND TRADEMARK OFFICE
CERTIFICATE OF CORRECTION

PATENT NO.   : 5,591,450
DATED        : Jan. 7, 1997
INVENTOR(S)  : Claudio CAVAZZA, et al.

It is certified that error appears in the above-indentified patent and that said Letters Patent is hereby corrected as shown below:

On the title page, Item [73], the Assignee, should read:

--Avantgarde S.p.A., Rome, Italy--

Signed and Sealed this

Twenty-fifth Day of March, 1997

Attest:

BRUCE LEHMAN

*Attesting Officer*   *Commissioner of Patents and Trademarks*